United States Patent [19] [11] 4,335,866
Bujan [45] Jun. 22, 1982

[54] FLOW CONTROL DEVICE

[75] Inventor: Albert F. Bujan, Waukegan, Ill.

[73] Assignee: Abbott Laboratories, North Chicago, Ill.

[21] Appl. No.: 277,309

[22] Filed: Jun. 25, 1981

Related U.S. Application Data

[62] Division of Ser. No. 77,456, Sep. 20, 1979, Pat. No. 4,285,492.

[51] Int. Cl.³ .......................... F16K 7/06; A61M 5/14
[52] U.S. Cl. .......................................... 251/9; 251/6; 251/7
[58] Field of Search ................. 251/6, 7, 9; 24/115 L, 24/132 WL, 134 KB

[56] References Cited

U.S. PATENT DOCUMENTS

| 1,055,552 | 3/1913 | Payne | 251/9 |
| 2,483,954 | 10/1949 | Weiss | 251/9 |
| 2,595,511 | 5/1952 | Butler | 251/6 |
| 3,099,429 | 7/1963 | Broman | 251/6 |
| 3,813,077 | 5/1974 | Kolic | 251/9 |
| 3,828,822 | 8/1974 | Witte | 251/9 |
| 3,960,149 | 6/1976 | Bujan | 251/6 |
| 4,285,492 | 8/1981 | Bujan | 251/9 |

FOREIGN PATENT DOCUMENTS

| 432785 | 3/1948 | Italy | 251/9 |
| 330964 | 6/1958 | Switzerland | 251/9 |
| 585867 | 3/1977 | Switzerland | 251/9 |
| 412424 | 8/1974 | U.S.S.R. | 251/9 |

Primary Examiner—H. Jay Spiegel
Attorney, Agent, or Firm—Robert L. Niblack; Robert S. Beiser

[57] ABSTRACT

An improved clamp for regulating the flow of fluid through a length of flexible tubing comprising a clamp body for supporting the tubing, having opposing walls extending from the surface of the clamp body so as to present a passage for the flexible tubing. A platen is mounted between the walls for contacting the tubing. Guide surfaces are arranged in the walls with a roller positioned within the guide surfaces. The platen is movably positioned between the roller and the flexible tubing so as to present a compression surface against the tubing along the path of travel of the roller. The combination of the platen and the roller exerts a compressive force against the tubing and distributes the force over a wide area of the tubing so as to prevent permanent deformation of the tubing. This compressive force constricts the tubing and thereby regulates flow of liquid therethrough. The improvement comprises a second roller also positioned within the clamp body, so as to exert an additional compressive force upon the platen and thereby against the tubing. As a result through use of the first and second rollers, separate controls are provided for coarse and fine regulation of the flow of liquid through the tubing.

11 Claims, 13 Drawing Figures

U.S. Patent Jun. 22, 1982 Sheet 1 of 3 4,335,866
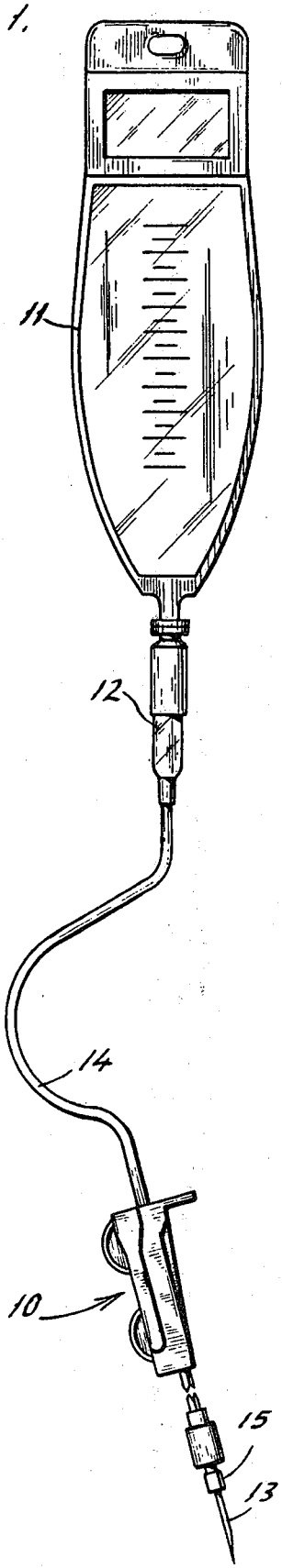
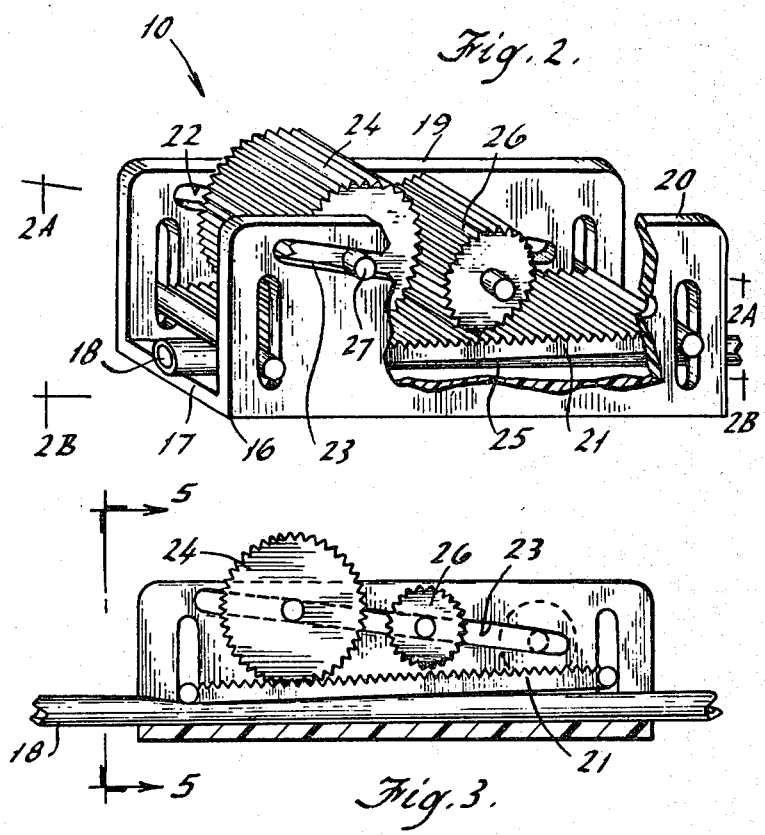
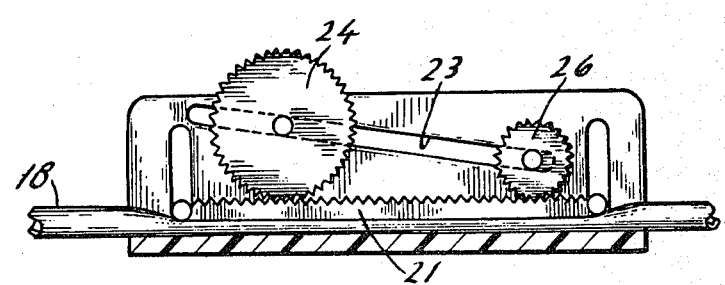
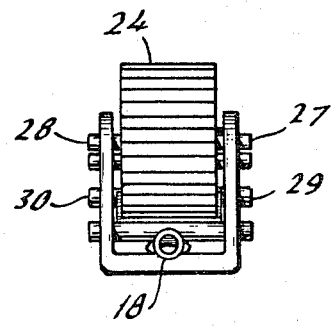

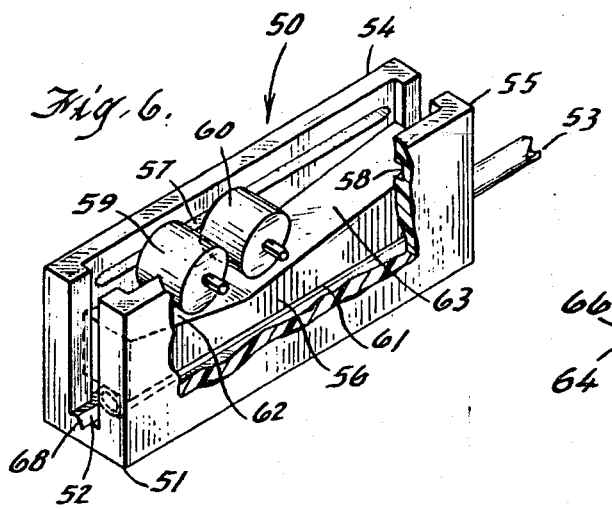
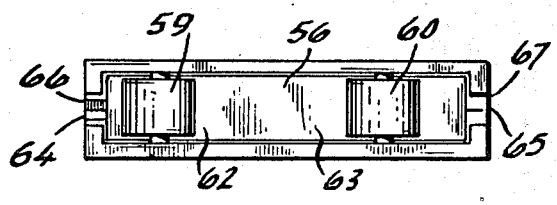
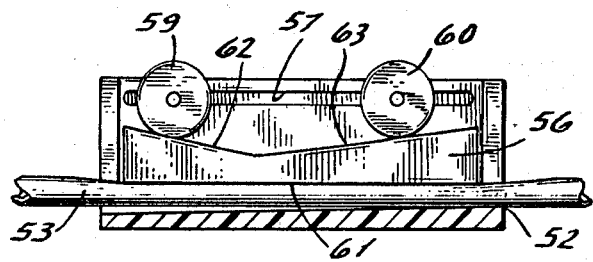
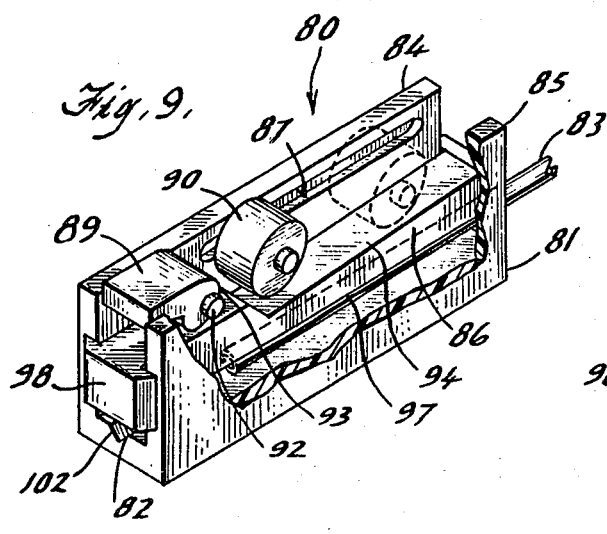
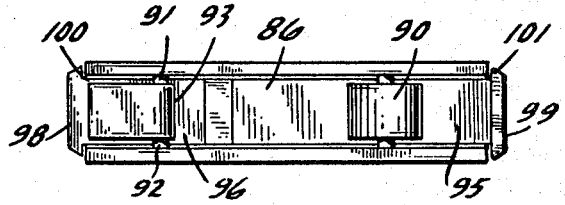
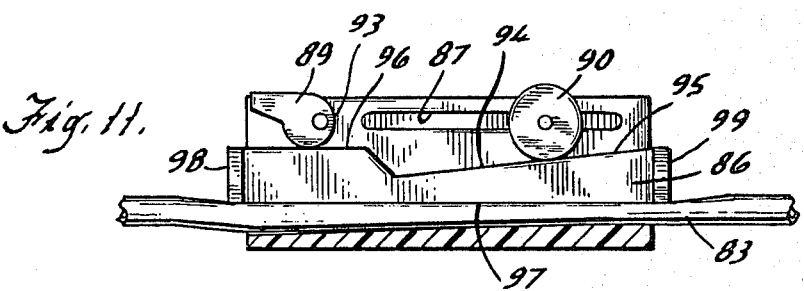

FLOW CONTROL DEVICE

This is a division of application Ser. No. 77,456, filed Sept. 20, 1979, now U.S. Pat. No. 4,285,492.

BACKGROUND OF THE INVENTION

This invention relates generally to flow control devices and more particularly to a combined clamp and flow control which exerts a compressive force on a length of tubing over a wide area so as to prevent permanent crimping of the tubing, and which provides separate controls for gross and fine regulation of the flow of liquid through the tubing.

Clamping devices, or fluid flow control units of the type concerned with in this invention, are disclosed in U.S. Pat. Nos. 2,595,511 and 3,099,429. In these units, rollers are employed to exert an increasing or decreasing force upon flexible tubing so as control the flow of fluid therethrough.

U.S. Pat. No. 3,960,149, of the present inventor discloses a combined clamp and flow control member which utilizes a rotatable member movably positioned within a clamp so as to exert a compressive force against a platen and thereby against a piece of flexible tubing. As a result, flow of liquid through the tubing is controlled. The present invention represents a distinct improvement over applicant's previous patent in that separate means are provided for coarse and fine regulation of the flow of liquid through the tubing. As a result, a greater number of incremental flow control settings are available than similar devices in the prior art.

SUMMARY OF THE INVENTION

The foregoing advantages are accomplished and the shortcomings of the prior art are overcome by the present combined clamp and flow control member. The device has a clamp body with a surface for supporting a length of flexible tubing and for presenting a passage for the tubing. A platen is movably positioned between the walls of the clamp body for contacting the tubing. Guide surfaces are arranged in the walls of the clamp and a first rotatable member is positioned in the guide surfaces so as to be movable along the guide surfaces. The platen is constructed and arranged to be movably positioned between the first rotatable member and the tubing. The platen presents a compression surface for the tubing along the path of travel of the first rotatable member. It also cooperates with the first rotatable member to exert an incremental compressive force on the tubing and by means of the platen, to distribute the compressive force over a wide area of the tubing. As a result, coarse regulation of the flow of liquid through the tubing is provided.

A second rotatable member is positioned within the clamp body and is arranged to cooperate with the first rotatable member and the platen to exert an additional incremental compressive force upon the tubing. By this it is meant, in a preferred embodiment, that the first rotatable member exerts an initial force upon the platen and that the second rotatable member is used to exert an additional compressive force, preferably by pivoting the platen, in order to further compress the platen against the tubing. As a result, means are provided for regulating in minute or fine quantities, the flow of liquid through the flexible tubing.

In a preferred embodiment the previously mentioned first rotatable member is a roller having pins extending from it and the previously mentioned guide surfaces comprise one or more (preferably two) parallel grooves with the pins positioned in the grooves. The grooves in this embodiment have an axis positioned to intersect the axis of the supporting surface for the tubing. The roller is mounted on the pins so as to be rotatable within the grooves. As a result, the roller may be moved longitudinally along the grooves so as to compress the platen against the tubing. In a preferred embodiment, the second rotatable member also comprises a roller having pins extending therefrom with the pins positioned in the previously mentioned parallel grooves. The second rotatable member has a smaller radius than the first rotatable member, in a preferred embodiment, so that when both the first and second rotatable members are moved along the guide surfaces, the first rotatable member initially contacts the platen, thereby compressing the tubing. The flow of liquid through the tubing is thus constricted. Movement of the second rotatable member after such initial compression is effective to pivot the platen further against the tubing. Additional compression is thus incrementally applied to the platen, and the flow of liquid through the tubing is thus further regulated in minute or fine quantities. In other words, the first rotatable member acts as a fulcrum upon the platen so that when the second rotatable member moves, the platen pivots against the tubing, compressing it.

In an alternative embodiment of the invention, the previously mentioned platen includes a first contact surface adapted to abut the first rotatable member. Also included is a second contact surface adapted to abut the second rotatable member. In a preferred embodiment, the previously mentioned second contact surface is angularly disposed (at an angle) from the first contact surface. As a result, the platen may be depressed against the tubing through the action of the first rotatable member, the second rotatable member, or the combination of the first and second rotatable members. Thus, a multiplicity of operating settings and corresponding rates of flow of liquid are provided.

In another alternative embodiment of the invention, the previously mentioned first rotatable member may comprise a cam having pins extending therefrom into the opposing walls of the clamp body. The pins support the cam. In a first operating position, the extending surface of the cam pushes against the platen thereby compressing it against the tubing. The cam is rotatable within the cavity walls to a variety of operating positions including a second operating position in which compression of the tubing by the platen is released.

In additional embodiments of the invention, the first contact surface or the second contact surface, or both, may be angularly disposed from the compression surface of the bottom of the platen. As a result, horizontal movement of the first or second rotatable members relative to the support surface causes the platen to pivot, thereby depressing the platen against the tubing and compressing same.

In an additional embodiment of the invention the previously mentioned platen includes a plurality of flanges extending from it. The flanges may be disposed in a variety of guide surfaces in the clamp walls so as to both retain the platen within the clamp and direct the movement of the platen towards the tubing.

In order to accommodate the previously mentioned tubing, the supporting surface of the clamp has a groove extending along its longitudinal axis for accommodating the tubing. In a preferred embodiment the groove is U-shaped. The groove also may be U-shaped transversely to the supporting surface and V-shaped parallel to the supporting surface, V-shaped transversely and parallel to the supporting surface or simply an inclined plane. Alternatively, the clamp body may be U-shaped defining generally parallel walls in an interconnecting base so as to accomplish the same effect as the previously mentioned U-shaped groove.

In a preferred embodiment of the invention, the first rotatable member, the second rotatable member and the platen include toothed surfaces. The toothed surfaces facilitate precise positioning of the first and second rotatable members, and also facilitate maintaining the first and second rotatable members in a desired position. As a result, more precise control of the flow of liquid through the tubing is provided.

BRIEF DESCRIPTION OF THE DRAWINGS

FIG. 1 of the drawings is a side view, partially broken away, of a flow control clamp member operatively associated with a parenteral administrative unit.

FIG. 2 of the drawings is a perspective view, partially broken away, of the flow control clamp of FIG. 1.

FIG. 3 of the drawings is a side cutaway view of the flow control clamp of FIG. 1, showing in particular a first rotatable member positioned so as to exert a compressive force on the flexible tubing running through the clamp thereby compressing the tubing and constricting the flow of liquid through the tubing.

FIG. 4 of the drawings is a side cutaway view of the flow control clamp as shown in FIG. 1, showing in particular both first and second rotatable members positioned so as to exert a compressive force upon a platen, thereby compressing the flexible tubing running through the clamp and constricting the flow of liquid through the tubing.

FIG. 5 of the drawings is an end view of the flow control clamp of FIG. 1 taken along line 5—5 of FIG. 3.

FIG. 6 of the drawings is a perspective view, partially broken away, of an alternative embodiment of the invention showing in particular a flow control clamp having first and second rotatable members of approximately the same size, guide surfaces within the opposing walls of the flow control clamp running horizontally along the length of the clamp, and first and second contact surfaces formed on the compression platen.

FIG. 7 of the drawings is a top view of the flow control clamp as shown in FIG. 6.

FIG. 8 of the drawings is a side cutaway view of the flow control clamp of FIG. 6.

FIG. 9 of the drawings is a perspective view, partially broken away, of an additional embodiment of the invention, showing in particular a first rotatable member comprising a cam and a second rotatable member comprising a roller positioned over a compression platen having a horizontal first contact surface and a second contact surface angularly displaced from the first contact surface.

FIG. 10 of the drawings is a top view of the flow control clamp of FIG. 9.

FIG. 11 of the drawings is a side cutaway view of the flow control clamp of FIG. 9 showing in particular the second rotatable member positioned so as to compress the platen against the flexible tubing thereby constricting the flow of liquid through the tubing.

DESCRIPTION OF THE PREFERRED EMBODIMENT

Figure 12:
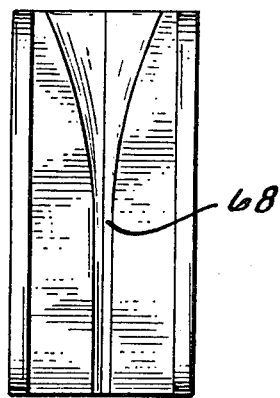
FIG. 12 of the drawings is a top plan view of an additional embodiment of the invention in which the base or floor of the clamp body is V-shaped in cross section.

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiments illustrated.

Flow control device 10, as shown in FIG. 1, is used in conjunction with a parenteral administration unit composed of a solution container 11 and a drip chamber 12 which is interconnected to a hypodermic needle 13 by means of a length of tubing 14 connected to a needle adapter 15.

As best shown in FIG. 2, the combined flow control and clamp device 10 comprises a clamp body 16 having a surface 17 for supporting a length of flexible tubing 18. Opposing walls 19 and 20 extend from surface 17 and present a passage for tubing 18. A platen 21 is mounted between walls 19 and 20 and is designed for contacting tubing 18. Guide surfaces 22 and 23 are arranged in walls 19 and 20, respectively. A first rotatable member 24 is positioned within guide surfaces 22 and 23. Platen 21 is arranged to be movably positioned between first rotatable member 24 and tubing 18. Platen 21 presents a compression surface 25 against tubing 18 substantially along and over the path of travel of first rotatable member 24 along guide surfaces 22 and 23. As a result of the movement of first rotatable member 24 along this path of travel, platen 21 exerts a compressive force in increasing increments based on the position of first rotatable member 24 against tubing 18. Compression surface 25 distributes this compressive force over a wide area of tubing 18 so as to prevent permanent deformation of tubing 18 from said compression.

The present invention represents a distinct improvement over the prior art in the use of a second rotatable member 26 positioned within clamp body 16 and arranged so as to exert an additional compressive force upon tubing 18. As a result, separate control is provided for minute or fine regulation of the flow of liquid through flexible tubing 18. In a preferred embodiment, first rotatable member 24 is a roller having pins 27 and 28 (best shown in FIG. 5) positioned within guide surfaces 22 and 23. In a preferred embodiment, guide surfaces 22 and 23 are a series of parallel grooves along opposing walls 19 and 20. Guide surfaces 22 and 23 are positioned along axis 2A which is angled to intersect axis 2B of supporting surface 17. As mentioned previously, first rotatable member 24 is designed to rotate within guide surfaces 22 and 23 and to thereby move longitudinally along guide surfaces 22 and 23 so as to compress platen 21 against tubing 18. As a result, tubing 18 is constricted and the flow of liquid through tubing 18 is regulated. Similarly, in a preferred embodiment, second rotatable member 26 is a roller having pins 29 and 30 (best seen in FIG. 5) extending from it. Pins 29 and 30 are positioned in guide surfaces 22 and 23 so as to allow movement of second rotatable member 26 thereby compressing platen 21 against tubing 18.

As best seen in FIG. 3 of the drawings, second rotatable member 26 has a smaller radius than first rotatable member 24. When first rotatable member 24 and second rotatable member 26 are moved along guide surfaces 22 (not shown) and 23, first rotatable member 24 initially contacts platen 21. Such contact causes platen 21 to pivot against tubing 18 thereby compressing tubing 18 and constricting the flow of liquid therethrough.

As best seen in FIG. 4 of the drawings, following the initial movement of first rotatable member 24 so as to compress platen 21 against tubing 18, movement of second rotatable member 26 along guide surfaces 22 (not shown) and 23 and against platen 21 further compresses platen 21 against tubing 18. However, in this instance, first rotatable member 24 is acting as a fulcrum upon platen 21 and second rotatable member 26 is pivoting platen 21 against tubing 18. Therefore, the movement of second rotatable member 26 increases or decreases the flow of liquid in tubing 18 in relatively small increments. Thus, separate means are provided for coarse and fine regulation of the flow of liquid through tubing 18. Alternatively, second rotatable member 26 may be positioned initially against platen 21 so as to compress platen 21 against tubing 18. First rotatable member 24 may then be moved along guide surfaces 22 and 23 so as to further pivot platen 21 against tubing 18, thereby further constricting tubing 18. In this way, the coarse regulation of liquid flow through tubing 18 may be regulated by second rotatable member 26, and the fine regulation of liquid flow through tubing 18 may be regulated by first rotatable member 24.

As best seen in FIG. 6 of the drawings, in an alternative embodiment, flow control device 50 comprises a clamp body 51 having a surface 52 for supporting a length of flexible tubing 53. Clamp body 51 includes opposing walls 54 and 55 extending from surface 52 and presenting a passage for tubing 53. A platen 56 is mounted between walls 54 and 55 and is designed for contacting tubing 53. Guide surfaces 57 and 58 are arranged in opposing walls 54 and 55. First rotatable member 59 and second rotatable member 60 are movably positioned within guide surfaces 57 and 58. Platen 56 is arranged to be movably positioned between, on the one hand, first rotatable member 59 and second rotatable member 60 and, on the other hand, tubing 53. Platen 56 presents a compression surface 61 against tubing 53. One of the differences of the embodiment illustrated in FIG. 6 from that shown in FIG. 1 is the inclusion of first contact surface 62 and second contact surface 63 on that portion of platen 56 which faces first rotatable member 59 and second rotatable member 60. First contact surface 62 and second contact surface 63 are angularly disposed from each other whereby movement of either the first rotatable member 59, the second rotatable member 60 or the combination of both may be used to press platen 56 against tubing 53. As a result a wide multiplicity of operating settings and corresponding rates of flow of liquid through tubing 53 are provided.

As best seen in FIG. 7, flanges 64 and 65 extend from platen 56 and are disposed within grooves 66 and 67. Again, flanges 64 and 65 are used to guide the movement of platen 56 within clamp body 51 as well as to maintain platen 56 within the clamp body.

As shown in FIG. 8 of the drawings, first contact surface 62 is angularly disposed from compression surface 61 and from guide surfaces 57 and 58 (not shown). As a result, when first rotatable member 59 is moved horizontally along guide surfaces 57 and 58 toward flange 64, platen 56 is pivoted against tubing 53, compressing it. Similarly, second contact surface 63 is angularly disposed from compression surface 61 and from guide surfaces 57 and 58. Therefore, movement of second rotatable member 60 toward flange 65 accomplishes similar pivoting of platen 56.

As best seen in FIG. 9 of the drawings, in an alternative embodiment, flow control clamp 80 again comprises a clamp body 81, a support surface 82 for tubing 83, opposing walls 84 and 85, a platen 86 positioned between opposing walls 84 and 85, guide surfaces 87 and 88 (not shown), first rotatable member 89 and second rotatable member 90. However, in the embodiment illustrated, first rotatable member 89 comprises a cam mounted between opposing walls 84 and 85 by means of pins 91 (not shown; best seen in FIG. 10 of the drawings) and 92. Cam 89 is shown in the second operating position in which platen 86 is compressed against tubing 83. However, cam 89 is rotatable to a first operating position in which surface 93 of cam 89 is moved toward platen 86 which in turn releases compression of tubing 83.

As shown in FIG. 11 of the drawings, second contact surface 95 is angularly disposed from both first contact surface 96, compression surface 97 and guide surface 87. As a result, when second rotatable member 90 is moved along guide surface 87 toward flange 99, platen 86 is pivoted against tubing 83. Alternatively, cam 89 may be rotated against contact surface 96 so as to pivot platen 86 against tubing 83. Each of these operations may be performed independently or in combination so as to sufficiently compress tubing 83 to the degree required to produce the desired rate of flow of liquid. As further shown in FIG. 11 of the drawings, platen 86 includes flange members 98 and 99 extending therefrom for guiding platen 86.

As best seen in FIG. 10, flange members 98 and 99 are disposed in guide surfaces 100 and 101 and are used to guide platen 86 within clamp body 81 as well as to retain the platen 86 within clamp body 81.

As best seen in FIGS. 6 and 9 of the drawings, supporting surfaces 52 and 82 may have a groove such as grooves 68 and 102, respectively, disposed on support surfaces 52 and 82. Grooves 68 and 102 are designed for accommodating tubing. As shown, grooves 68 and 102 are V-shaped in configuration. As best seen in FIG. 12 of the drawings, groove 68 may also be V-shaped in cross-section so as to facilitate insertion of tubing 53.

Figure 13:
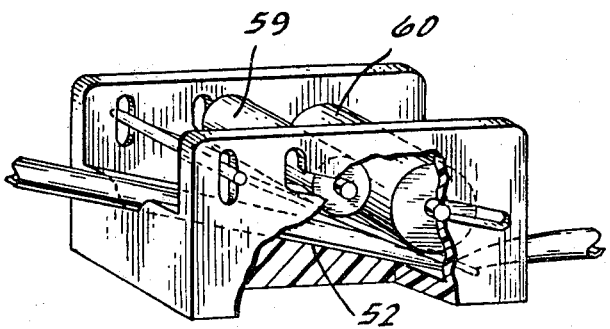
FIG. 13 of the drawings is a perspective view of an additional embodiment of the invention in which the base or floor of the clamp body is constructed as an inclined plane.

As further seen in FIG. 13 of the drawings, support surface 52 may be in the form of an inclined plane so as to eliminate the requirements for having an angularly displaced contact surface on platen 56. Additionally, groove 68 may be U-shaped, in order to facilitate insertion and compression of tubing 53.

In a preferred embodiment, flow control clamp 10 is constructed of a semirigid plastic material, preferably polypropylene. If desired, other polyolefin materials such as nylon, methylmethacrylate, polycarbonates, etc. can be utilized. A preferred method of manufacture is injection molding. However, other materials and manufacturing methods commonly known in the art may be utilized.

The above-described specific embodiments of this invention have been set forth for the purpose of illustration. It will be apparent to those skilled in the art that various modifications may be made in the structure of this tubing flow control clamp without departing from the principles of this invention as pointed out and disclosed herein. For that reason, it is not intended that the invention should be limited other than by the scope of the appended claims.

We claim:

1. A tubing clamp for regulating flow of fluid through a length of flexible tubing comprising:
   a clamp body defining a surface for supporting a length of flexible tubing having a longitudinal axis;
   opposing walls extending from said support surface and presenting a passage for said tubing;
   a platen mounted between said walls for contacting said tubing;
   guide surfaces arranged in said walls;
   a first rotatable member positioned to be guided by said guide surfaces;
   said platen constructed and arranged to be movably positioned between said first rotatable member and said tubing;
   said platen presenting a compression surface against said tubing substantially along and over the path of travel of said first rotatable member, and cooperating with said first rotatable member to exert an incremental compressive force on said tubing and by means of said platen to distribute the compressive force of said first rotatable member over a wide area of said tubing including a substantial distance along its longitudinal axis; and
   a second rotatable member operatively positioned within said clamp body and arranged to cooperate with said first rotatable member and said platen to exert an incremental compressive force upon said tubing whereby said first rotatable member and said second rotatable member provide separate control means for coarse and fine regulation of said flow of liquid through said flexible tubing;
   said second rotatable member comprises a cam having oppositely disposed pins extending therefrom, said pins extending into said opposing walls so as to support said cam; said cam in a first operating position being effective to compress said platen against said tubing; said cam being rotatable to a second operating position in which said compression of said tubing by said platen is released;
   said first rotatable member comprising a roller having pins extending therefrom with said pins positioned in said guide surfaces; said cam having a smaller radius than said first rotatable member whereby movement of said first rotatable member along said guide surfaces and movement of said cam in said supporting walls is effective to contact said first rotatable member initially against said platen so as to pivot said platen against said tubing thereby compressing said tubing and consequently constricting said flow of said liquid through said tubing; movement of said cam against said platen being effective to further compress said platen against said tubing thereby further compressing said tubing so as to incrementally increase or decrease said flow of said liquid in minute quantities.

2. The tubing clamp as defined in claim 1 in which said first rotatable member is effective to act as a fulcrum upon said platen thereby facilitating said pivoting of said platen against said tubing upon movement of said second rotatable member against said platen.

3. The tubing clamp as defined in claim 1 in which said platen includes a first contact surface adapted to abut said first rotatable member whereby rotation of said first rotatable member is effective to depress said platen against said tubing, and a second contact surface adapted to abut said second rotatable member whereby movement of said second rotatable member is effective to incrementally pivot said platen, thereby angularly depressing said platen against said tubing.

4. The tubing clamp as defined in claim 3 wherein said second contact surface is angularly disposed from said first contact surface whereby said platen is adapted to be depressed against said tubing by means of said first rotatable member, said second rotatable member or the combination of said first and second rotatable members so as to provide a multiplicity of operating settings and corresponding rates of flow of said liquid through said tubing.

5. The tubing clamp as defined in claim 3 or 4 in which said first contact surface is angularly disposed from said compression surface whereby horizontal movement of said first rotatable member relating to said support surface is effective to incrementally pivot said platen thereby angularly depressing said platen against said tubing.

6. The tubing clamp as defined in claim 1 wherein said platen includes a plurality of flange members extending from said platen and disposed within said guide surfaces so as to retain said platen within said clamp body and to direct the movement of said platen within said clamp body.

7. The tubing clamp as defined in claim 1 wherein said support surface has a groove extending along its longitudinal axis for accommodating said length of tubing.

8. The tubing clamp as defined in claim 7 wherein said groove is of a U-shaped configuration extending transversely to the supporting surface and having a V-shaped configuration parallel to the supporting surface.

9. The tubing clamp as defined in claim 7 wherein said groove is a V-shaped configuration extending both transversely and parallel to the supporting surface.

10. The tubing clamp as defined in claim 1 wherein said surface for supporting said length of tubing is defined by a base portion presenting an inclined plane.

11. The tubing clamp as defined in claim 1 in which said clamp body comprises a generally U-shaped body section defining generally parallel wall members and an interconnecting base portion.

* * * * *